(12) United States Patent
Oldenburg et al.

(10) Patent No.: US 8,822,209 B2
(45) Date of Patent: Sep. 2, 2014

(54) DISPOSABLE SPINNER FLASK

(75) Inventors: Kevin R. Oldenburg, Spokane Valley, WA (US); Andrew B. Holt, Coeur D'Alene, ID (US); Robert L. Weeks, Spokane Valley, WA (US)

(73) Assignee: Brooks Automation, Inc., Chelmsford, MA (US)

( * ) Notice: Subject to any disclaimer, the term of this patent is extended or adjusted under 35 U.S.C. 154(b) by 1187 days.

(21) Appl. No.: 12/171,984

(22) Filed: Jul. 11, 2008
(Under 37 CFR 1.47)

(65) Prior Publication Data

US 2009/0176301 A1    Jul. 9, 2009

Related U.S. Application Data

(60) Provisional application No. 60/949,465, filed on Jul. 12, 2007.

(51) Int. Cl.
| | |
|---|---|
| *C12M 3/00* | (2006.01) |
| *C12M 1/12* | (2006.01) |
| *C12M 1/00* | (2006.01) |
| *C12M 1/24* | (2006.01) |
| *C12M 1/06* | (2006.01) |

(52) U.S. Cl.
CPC ............. *C12M 23/28* (2013.01); *C12M 23/08* (2013.01); *C12M 27/02* (2013.01)
USPC ........ 435/302.1; 366/242; 366/244; 366/247; 435/297.1

(58) Field of Classification Search
CPC .... B01F 7/0025; B01F 7/1675; B01F 3/0827; B01F 7/1635; B01F 7/1645; C12M 27/02; C12M 27/20; C12M 29/04; C12M 23/34; C12M 25/02; C12M 23/24; C12M 23/05

USPC ................ 435/297.1; 366/242, 244, 247, 373
See application file for complete search history.

(56) References Cited

U.S. PATENT DOCUMENTS 3,649,465 A    3/1972   Scharf et al.
5,267,791 A  * 12/1993  Christian et al. .............. 366/249
(Continued)

FOREIGN PATENT DOCUMENTS

| DE | 19922912 A1 | 11/2000 |
|---|---|---|
| EP | 0752470 A2 | 1/1997 |
| WO | 03006633 A1 | 1/2003 |

OTHER PUBLICATIONS

Sigma-Aldrich, "Spinner Flasks," retrieved Jul. 11, 2008, http://www.sigmaaldrich.com/catalog/search/TablePage/9577902, 4 pages.

*Primary Examiner* — Michael Hobbs
(74) *Attorney, Agent, or Firm* — Seed IP Law Group PLLC

(57) ABSTRACT

A disposable spinner flask includes an asymmetric container, a lid, and a spinning mechanism. The container can be sealingly coupled to the lid, which includes an access port and a cap configured to be coupled to the access port for preventing bacteria, viruses, and fungi from passing therethrough while allowing air to flow between the container and a surrounding environment. The lid may include a structure for retaining the cap when the cap is removed. The spinning mechanism can include a shaft, at least one blade, and a magnetic device. Further, the spinning mechanism can include a receptacle that fixedly receives the magnetic device toward an end of the blade assembly, the magnetic device configured to rotate when subjected to an external magnetic force.

28 Claims, 5 Drawing Sheets

(56) References Cited

U.S. PATENT DOCUMENTS

| | | | |
|---|---|---|---|
| 6,086,240 A * | 7/2000 | Murphy | 366/147 |
| 6,109,780 A * | 8/2000 | Lesniak | 366/253 |
| 6,991,933 B1 | 1/2006 | Upton et al. | |
| 2005/0148068 A1* | 7/2005 | Lacey et al. | 435/297.5 |
| 2008/0131957 A1* | 6/2008 | Ryan et al. | 435/289.1 |

* cited by examiner

DISPOSABLE SPINNER FLASK

This application claims the benefit under 35 U.S.C. §119(e) of U.S. Provisional Patent Application No. 60/949,465 filed Jul. 12, 2007, where this provisional application is incorporated herein by reference in its entirety.

BACKGROUND

1. Technical Field

The present disclosure generally relates to laboratory apparatus, and more particularly, to a disposable spinner flask.

2. Description of the Related Art

Spinner flasks are generally used for growing suspensions of mammalian cells and other organisms. As illustrated in FIG. 1, typically, conventional spinner flasks 10 have a lid 12 that threadedly closes a glass container 14, and three separate necks 16. Since the container 14 of most conventional spinner flasks is made from glass, it can be costly to purchase and/or replace the flask, for example, due to breakage. In addition, in order to reuse these flasks, they have to be thoroughly cleaned and then sterilized using one of several available methods. Cleaning these flasks is typically time, labor, and cost intensive. Reusing these flasks can pose a potential risk of cross contamination if cleaning and sterilization is not completely successful.

Attempts at providing a disposable spinner flask that is practical have generally been unsuccessful. For example, conventional spinner flasks marketed as being disposable typically continue to be expensive. Accordingly, disposing of such a flask after each use is not practical and does not solve the cost issues related to the non-disposable spinner flasks.

Additionally, conventional spinner flasks such as the flask 10 shown in FIG. 1, are typically symmetrical about their longitudinal axes, which makes it essentially impossible for a robot in an automated system to recognize radial orientation of the flask 10. Therefore, existing devices are not optimized for use in robotic automated cell culture systems. Additionally, the opposing necks 16 of these flasks 10, which provide limited access to the interior of the flask 10, are canted at an angle that makes it difficult to access the contents of the flask, and requires that the stirring mechanism stop prior to removal of sample from the flask. Once the stirring mechanism stops, the cells immediately begin to settle causing sampling errors when trying to obtain accurate cell counts.

BRIEF SUMMARY

According to one embodiment, a disposable spinner flask includes a container having a mouth and forming an interior volume, the container being shaped such that the interior volume includes a first portion and a second portion. The disposable spinner flask further includes a cover assembly configured to be sealingly coupled to the mouth of the container and including an access port allowing access to the second portion of the interior volume at all times including during operation of the disposable spinner flask. The container, the cover assembly, or both, can be symmetrical about only a single axis. The disposable spinner flask further includes a spinning mechanism positionable in the first portion of the interior volume, at least a portion of the spinning mechanism being rotatably mounted with respect to the container, at least when the cover assembly is coupled to the mouth of the container.

According to one aspect, the cover assembly includes a lid configured to be sealingly and removably coupled to the mouth of the container, and a cap configured to be coupled to the access port to cover the access port when the access port is not in use, the cap being configured to at least partially move away from the access port to allow access to the interior volume. The cap can also be removably coupled to the access port and the lid can further include a first structural feature configured to retain the cap when the cap is removed from the access port. Moreover, the cap may include a permeable membrane configured to prevent bacteria, viruses, and fungi from passing therethrough while allowing air exchange between the interior volume and a surrounding environment.

According to another aspect, the cover assembly includes a cap configured to cover the access port and have at least one of a pierceable septum and a split septum to allow access to the interior volume. Furthermore, the spinning mechanism may include at least one blade coupled to a magnetic device configured to rotate to induce rotation of the at least one blade when subjected to an external magnetic force. The spinning mechanism may further include a shaft having a first end and a second end, the shaft being coupled to the cover assembly toward the first end and to the at least one blade toward the second end.

In some embodiments, at least a portion of the container or cover assembly includes a teardrop cross-sectional shape.

According to another embodiment, a disposable spinner flask includes a container having a mouth and a base, the container forming an interior volume open toward the mouth and a structure for covering the container configured to be sealingly coupled to the mouth of the container and including an access port allowing access to the interior volume at all times including during operation of the disposable spinner flask, at least one of the covering structure and the container being asymmetric about at least one longitudinal axis. The disposable spinner flask further includes structure for spinning a content of the container positioned in the interior volume and rotatably mounted with respect to the container, at least when the covering structure is coupled to the mouth of the container.

According to yet another embodiment, a method of manufacturing a spinner flask includes forming a container that is asymmetric about at least one longitudinal axis and that defines an interior volume bound by a base and an interior wall extending from the base toward an open mouth. The method further includes forming a lid configured to sealingly cover the container, providing a spinning mechanism configured to be rotatably mounted in the interior volume, and forming an access port in the lid such that the access port has a central longitudinal axis substantially perpendicular to the base of the container.

According to one aspect, forming the access port includes positioning the access port such that the central longitudinal axis of the access port intersects the base of the container.

According to one aspect, the method further includes forming a cap for covering the access port when the access port is not in use, and forming a permeable membrane on the cap configured to prevent bacteria, viruses, and fungi from passing therethrough while allowing air exchange between the interior volume and a surrounding environment.

According to one aspect, the method further includes forming a retaining structure on the lid to retain the cap when the cap is removed from the access port.

DETAILED DESCRIPTION

Figure 2:
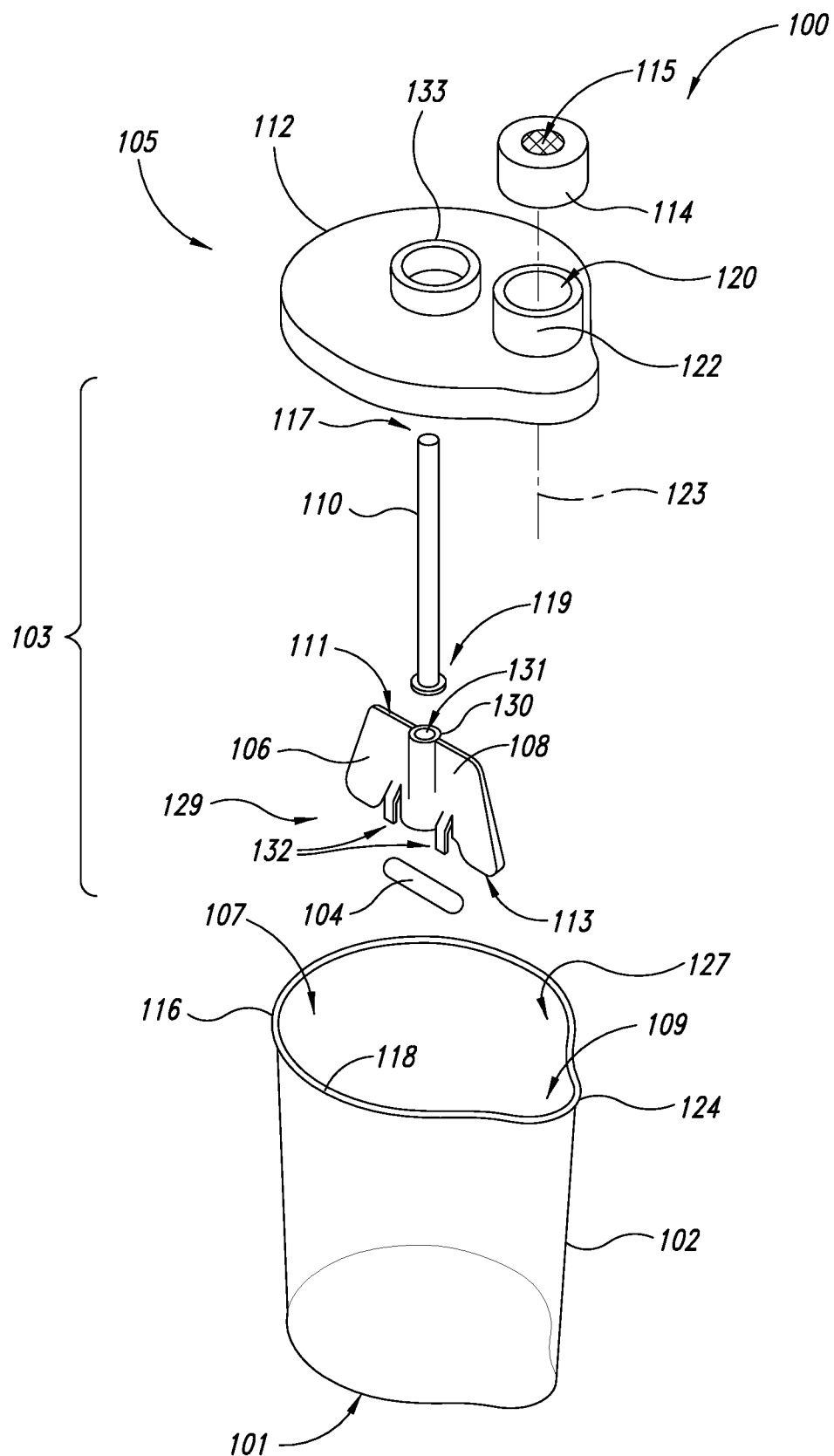
FIG. 2 is an exploded isometric view of a disposable spinner flask according to one embodiment.

FIG. 2 illustrates a disposable spinner flask 100 according to one embodiment. The disposable spinner flask 100 includes a container 102, a spinning mechanism 103, and a cover assembly 105.

In some embodiments, the shape of the disposable spinner flask 100 or a portion thereof is predetermined to facilitate automated handling of the disposable spinner flask 100. For example, the container 102 can be asymmetric about at least one longitudinal axis, or symmetric about only a single axis. In one embodiment, the container 102 includes an open mouth 116, a base 101, and a wall or walls 127 extending between the mouth 116 and the base 101. The container 102 further includes an asymmetric shape, such as a teardrop cross-sectional shape. In one aspect, the asymmetric shape can be at least partially formed by an extension 124 formed about the periphery of at least a portion of the container 102. For example, the extension 124 can extend from the mouth 116 toward the base 101 along at least a portion of the container 102. The asymmetric shape of the container 102 optimizes the disposable spinner flask 100 for use with automated cell culture systems because a robot or other automated system will be able to decipher radial orientation of the disposable spinner flask 100 based on the asymmetry. Orientation could also be achieved by using a symmetrical container 102 and an asymmetric lid 112.

In one embodiment, the spinning mechanism 103 includes a magnetic device 104, at least a first blade 106, or as illustrated, first and second blades 106,108, and an elongated shaft 110. The asymmetric shape, such as the teardrop shape, defines a first volume portion 107 and a second volume portion 109, the first volume portion 107 being larger than, and contiguous to, the second volume portion 109. In one aspect, the spinning mechanism 103 can be positioned in the first volume portion 107. Accordingly, another device can enter the container 102 in the second volume portion 109 while the blades 106, 108 are in motion, without interfering with the spinner blades 106, 108.

In some embodiments, the shape of the container is predetermined to facilitate a desired fluid flow characteristic. For example, the teardrop shape breaks up laminar flow and facilitates uninterrupted aspiration while the fluid is spinning.

In one embodiment, the cover assembly 105 includes a snap-on lid 112 and a cap 114. The snap-on lid 112 is configured to sealingly engage the mouth 116 of the container 102. For example, complementary structures can be formed on the container 102 and lid 112, respectively, such that the lid 112 engages the mouth 116 and forms a fluid tight seal. In one embodiment, the mouth 116 includes a retaining feature, such as a return lip 118, over which the perimeter of the lid 112 can snap and be retained for forming the fluid tight seal and preventing spillage in case the disposable spinner flask 100 is tipped on its side. The snap-on lid 112 may be fabricated from a flexible and/or resilient material such as plastics, rubbers, silicone, composites or any other suitable material that is capable of temporarily deforming to extend about the mouth 116 of the container 102.

Figure 1:
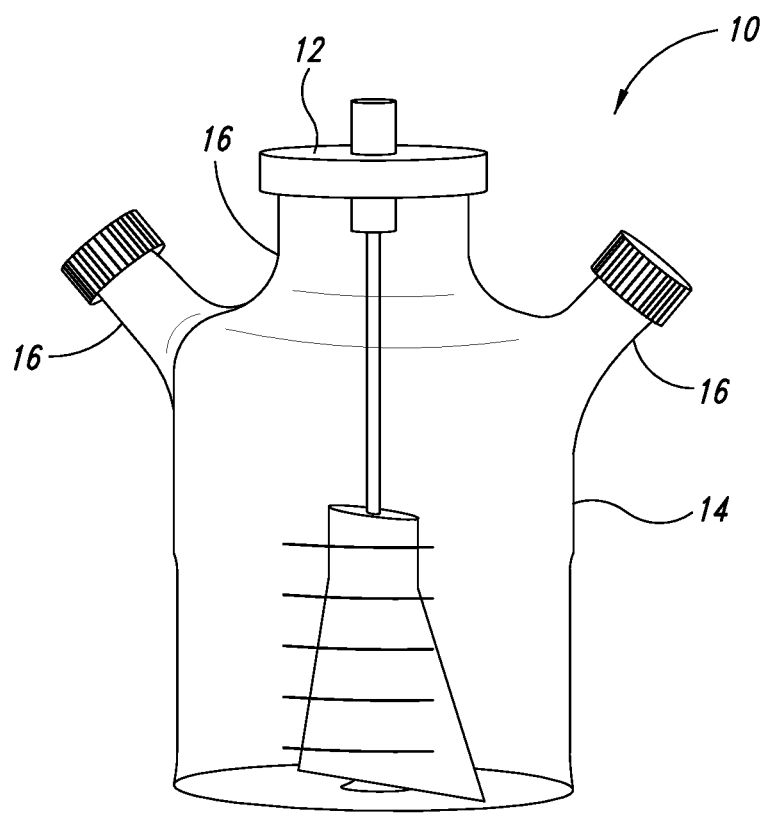
FIG. 1 is a front view of a conventional spinner flask according to the prior art.

Furthermore, the lid 112 includes at least one access port 120 that is configured to be sealed using the cap 114. In one aspect, the access port 120 includes a central longitudinal axis 123 that extends in at least a portion of the interior volume portion 109 formed by, or adjacent to, the extension 124. The central longitudinal axis 123 can extend substantially perpendicular to the base 101 of the container 102. In embodiments where the extension 124 longitudinally extends to the base 101 of the container 102, the central longitudinal axis 123 can be substantially perpendicular to, and intersect, the base 101. Accordingly, a user can easily access the contents of the container 102 while the spinning mechanism 103, or a portion thereof, is rotating, without interfering with the spinning mechanism 103 and without experiencing access difficulties associated with opposing angled necks 16 (FIG. 1) of conventional spinner flasks 10 (FIG. 1).

In one embodiment, the cap 114 includes at least one air vent 115 that prevents fungi, bacteria, and viruses from entering the container 102 while allowing an interior of the container to be in gaseous communication with a surrounding environment for allowing free air exchange therebetween. The cap 114 is configured to be removably coupled to the access port 120, for example via complementary coupling structures formed on the cap 114 and access port 120, respectively. In one embodiment, the access port 120 may comprise a lip 122 over which the cap 114 can snap. In another embodiment, the cap 114 may threadedly engage the access port 120. Furthermore, the cap 114 is configured to be removed for robotic or manual access to contents, such as a liquid contained within the container 102.

In embodiments in which the container 102 has a teardrop shape, the access port 120 may be positioned above a narrower portion of the teardrop shape such as the second volume portion 109. Accordingly, when the cap 114 is removed, either robotically or manually, the robotic device or other device can access the liquid in the second volume portion 109 of the container 102 while the blades 106, 108 are spinning, or when they have ceased spinning. In some embodiments the cap 114 can allow access through the port 120 while remaining attached to the lid 112, for example by pivotably attaching thereto or through a split septum or pierceable septum, as described in more detail further below. Alternatively in other embodiments, the lid 112 may be completely removable.

Furthermore, the lid 112 may include a structural feature 133 configured to retain the cap 114 while the latter is removed to reveal the access port 120. In such an embodiment, while removed, the cap 114 can be stored by being coupled to the structural feature 133. The structural feature 133 may include a slot, a protrusion, a tab, a vice feature, any combination thereof, or any other suitable shape or feature configured to engage a portion of the cap 114 to temporarily retain the cap 114.

When the spinner flask 100 is in use, the first and second blades 106, 108 rotate with the shaft 110 powered by the magnetic device 104, which can be positioned toward the base 101 of the container 102. Further, the first and second blades 106, 108 can be coupled on opposing lateral sides of a hub 130 formed therebetween. The blades 106, 108, and/or hub 130, have a first side 111 toward the shaft 110, and a second side 113, opposed to the first side 111. In one aspect, the shaft 110 can be rotatably coupled to the lid 112 toward a first end 117 of the shaft 110, while being fixedly coupled to the first and second blades 106, 108 toward a second end 119 of the shaft 110. In another aspect, the shaft 110 can be fixedly coupled to the lid 112 while being rotatably coupled to the first and second blades 106, 108. In one embodiment, the shaft 110 is compression fit toward its first end 117 into a fitting (not shown) on the underside of the lid 112. The hub 130 may include a cylindrical shape having a receptacle or opening 131 configured to receive the shaft 110 toward the second end 119 of the shaft 110.

Toward the second side 113 of the blades 106, 108, and/or hub 130, at least one coupling member 129 can be configured to couple the magnetic device 104 to the blades 106, 108. In one embodiment, the coupling member 129 includes at least one receptacle or slot 132, which is configured to securely and removably receive the magnetic device 104. When the apparatus is placed above or over an external magnetic stirring device (not shown), the magnetic device 104 begins to rotate in response to an external magnetic force, thereby facilitating rotation of the blades 106, 108 for culturing cells such as mammalian cells, plant cells, microorganisms, keeping other particulate matter in solution, and/or any other suitable use. The magnetic device 104 may rotate about an axis substantially parallel to a direction along which the shaft 110 is elongated. Moreover, the shaft 110 can be elongated in a direction substantially parallel to the longitudinal axis 123.

The hub 130 can also be hollow. In such embodiments, the second end 119 of the shaft 110 may include a magnetic element that is attracted to the magnetic device 104 positioned on the second side 113 of the blades 106, 108, and/or hub 130. Therefore, when the magnetic device 104 is snapped into place or otherwise secured in the at least one receptacle 132 on the second side 113 of the blades 106, 108, and/or hub 130, the magnetic attraction between the magnetic device 104 and the magnetic element toward the second end 119 of the shaft 110 maintains the shaft 110 coupled to the hub 130.

The container 102 can be fabricated from any material that is disposable and less costly than existing flasks, such as plastics, rubbers, silicone, glass, composites, any combination thereof, or any other suitable material. In one embodiment, components of the disposable spinner flask 100, such as the container 102 and/or the cover assembly 105 are formed from an at least partially transparent and/or translucent material, such as polycarbonate, such that a user can readily observe the contents of the container 102. For example, the container 102 can be molded from virgin polycarbonate, facilitating cost reduction while maintaining consumable strength. In one embodiment, the components of the disposable spinner flask 100 can be made from chemically tolerant LEXAN® polycarbonate. Furthermore, in embodiments in which the container 102 is plastic, the container 102 can be formed using an injection moldable plastic and an injection mold or could be blow molded.

The spinning mechanism 103, or portions thereof, can also be configured to be disposable and inexpensive. For example, the shaft 110 and first and second blades 106, 108 can be fabricated using a co-injection molding with injection moldable plastic or other material that lends to injection molding, for reducing the cost of fabrication and facilitating disposal of the shaft 110 and first and second blades 106, 108 after use.

The disposable spinner flask 100 can be sterilized if needed using vaporized hydrogen peroxide treatment, ethylene oxide treatment, and/or by autoclaving (i.e., use of temperature and pressure). Alternatively, the disposable spinner flask 100 can be disposed after one-time use or after more than one-time use, greatly reducing time-consuming and costly re-sterilization procedures.

Figure 3A:
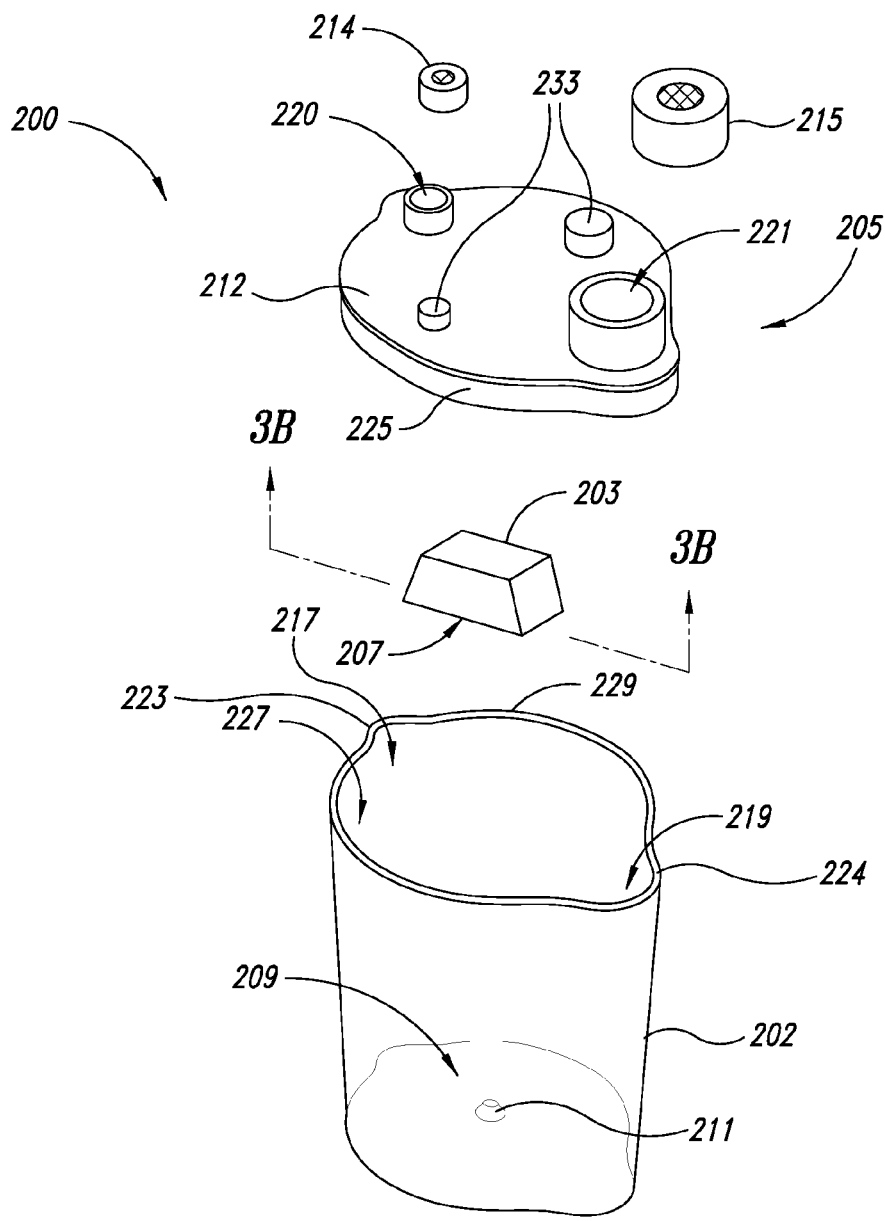
FIG. 3A is an exploded isometric view of a disposable spinner flask according to another embodiment.
Figure 3B:
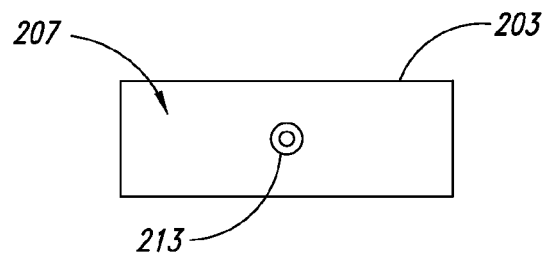
FIG. 3B is a bottom view of a portion of the disposable spinner flask of FIG. 3A.

In another embodiment as illustrated in FIGS. 3A and 3B, a disposable spinner flask 200 includes a container 202, a spinning member 203, and a cover assembly 205. In this embodiment, the spinning member 203 is a unitary magnetic device that can be shaped to induce a particular flow that is desired. In this manner a separate part that constitutes the blades is not necessary. The spinning member 203 includes a bottom surface 207 that is shaped to maintain an upright positioning of the spinning member 203. For example, the bottom surface 207 can have a flat rectangular shape that rotatably rests on a base 209 of the container 202. Maintaining the spinning member 203 in a particular position can be accomplished by the positioning of an external magnetic device that induces rotation of the spinning member 203.

In one aspect, as illustrated in FIGS. 3A and 3B, the base 209 of the container 202 and the spinning member 203 can respectively include complementary structural features 211, 213, which facilitate retention of the spinning member 203. For example, the spinning member 203 can include a depression, recess, or dimple configured to removably mount over a protrusion on the base 209, while allowing the spinning member 203 to rotate, to prevent lateral movement of the spinning member 203 when it is rotating.

Furthermore, in the illustrated embodiment of FIG. 3A, the container 202 and cover assembly 205 are mutually shaped to allow for simultaneous access to the interior of the container 202 through more than one access port. For example, the cover assembly 205 can include a lid 212 having two access ports 220, 221 that are positioned over two access areas 217, 219 formed in the container 202. The access areas 217, 219 can be formed by extensions 223, 224 in a periphery of the container 202. The cover assembly 205 can include two caps 214, 215 that can be coupled to the access ports 220, 221 to cover the access ports 220, 221, respectively. The cover assembly 205 can also include respective structural features 233 to which the caps 214, 215 can be engaged for being retained while the access ports 220, 221 are in use.

To facilitate an automation friendly configuration, the size and/or shape of each of the access areas 217, 219 can be different from one another to define an asymmetric exterior surface about the disposable spinner flask 200. Alternatively, the access areas 217, 219 can have substantially identical sizes and shapes, and be radially positioned such that the container 202 is asymmetric about at least one longitudinal axis.

The access areas 217, 219 are positioned to prevent interference of probes or other devices, such as thermometers, with the spinning member 203. Having more than one access port can be useful in allowing the user to obtain information about more than one property of the contents of the container 202 while the disposable spinner flask 200 is in operation. Furthermore, multiple access ports can facilitate taking samples of the contents from different areas in the container 202 for ascertaining the consistency of a mixture or of a property or quality of the contents in different portions thereof, and determine whether the contents have been sufficiently processed.

Figure 4:
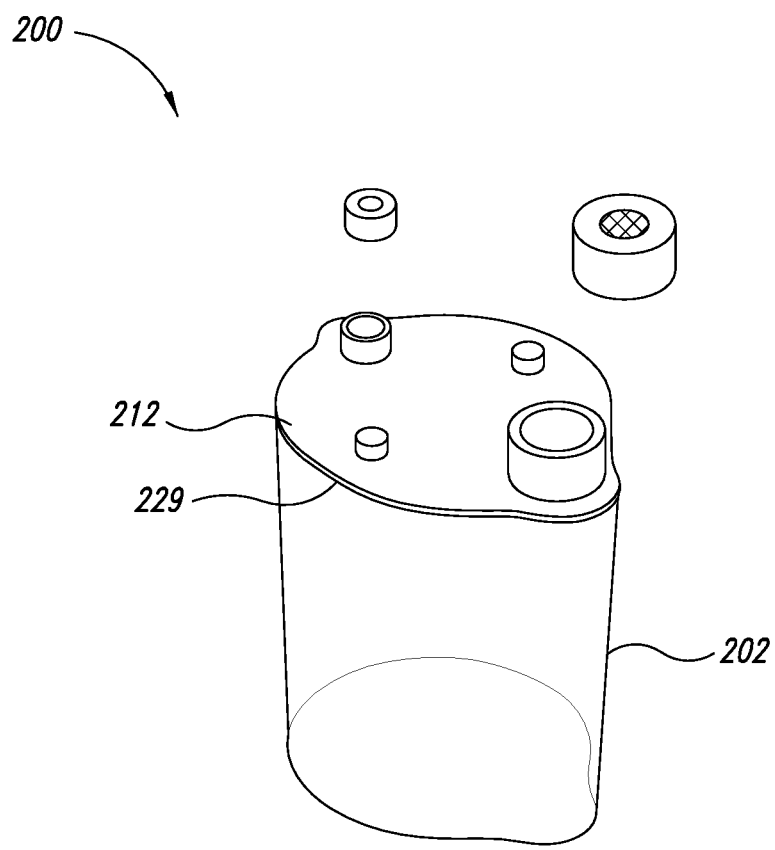
FIG. 4 is an isometric view of the disposable spinner flask of FIG. 3A.

In one aspect, the lid 212 can include a cylindrical projection 225 configured to sealingly fit contiguous to an interior wall or walls 227 of the container 202 toward a mouth 229 of the container 202. FIG. 4 illustrates the lid 212 coupled to the container 202 via the cylindrical projection 225 (FIG. 3A). Since in this embodiment, the lid 212 is coupled to the interior wall or walls 227 (FIG. 3A) of the container 202, it can form a flush external surface with the container 202 toward the mouth 229 of the container 202. Accordingly, automated systems or robots handling the disposable spinner flask 200 toward the mouth 229 can engage the disposable spinner flask 200 in proximity of the cover assembly 205 along the flush exterior surface.

Figure 5:
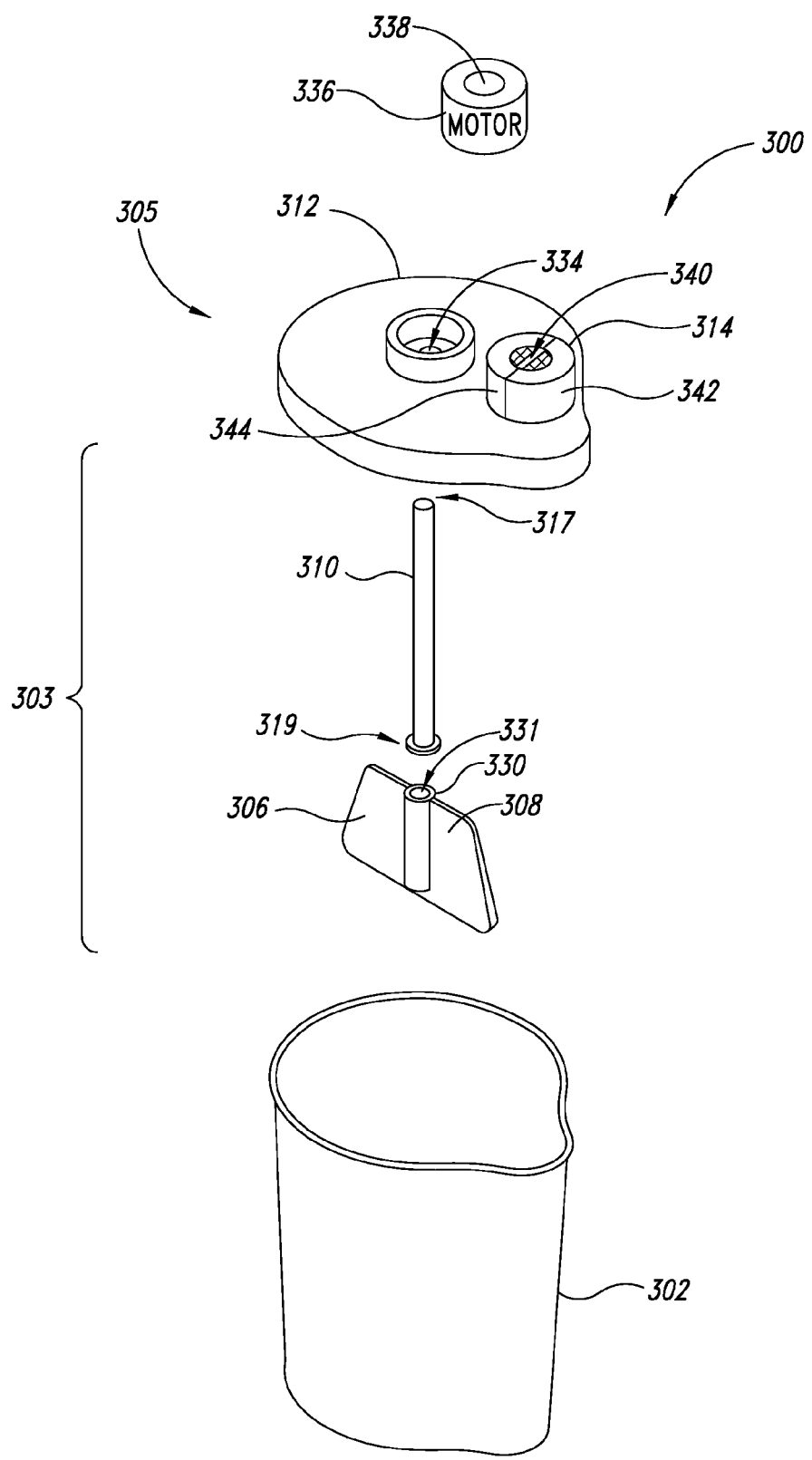
FIG. 5 is an exploded isometric view of a disposable spinner flask according to yet another embodiment.

Although the above embodiments have been described as incorporating a magnetic device to facilitate spinning, one of ordinary skill in the art will appreciate that other modes of inducing spinning are within the scope of the present disclosure. For example, as illustrated in FIG. 5, in another embodiment, a disposable spinner flask 300 includes a container 302, a spinning mechanism 303, and a cover assembly 305. In this embodiment, the spinning mechanism 303 includes two blades 306, 308 positioned on different or opposing sides of a hub 330, which is in turn coupled to a shaft 310 via a coupling structure 331. The shaft 310 includes a first end 317 and a second end 319, the second end 319 being coupled to the coupling structure 331, which can include a recess or a cavity configured to receive the shaft 310 toward the second end 319 thereof. In another aspect, the shaft 310, the first and second blades 306, 308, and the hub 330 can be fabricated from a unitary body of material.

Furthermore, the cover assembly 305 includes a lid 312, having an aperture 334 extending through a thickness thereof, and a motor 336. In the illustrated embodiment of FIG. 5, the shaft 310 has a length such that the shaft can extend through the aperture 334 in the lid 312 and be rotatably and removably coupled to the motor 336, which is positioned on an exterior side of the lid 312. To facilitate portability of the disposable spinner flask 300, the motor 336 can include a power source 338 that is also portable, such as a battery. However, in some embodiments, the power source can be stationary, such as a power plug supplying power to the motor 336 via a power cord. Since the motor 336 is removably coupled to the shaft 310, it can be removed and placed on a subsequent disposable spinner flask 300, when one is used and disposed. To prevent contamination of the contents of container 302, the motor 336 is sealingly coupled to the lid 312 over the aperture 334.

In one embodiment, the lid 312 can include a cap 314 configured to be coupled to an access port similar to the access ports 120, 221 discussed above in conjunction with FIGS. 2 and 3A. In this embodiment, the cap 314 can include a split or pierceable septum 340 through which the contents of the container 302 can be accessed while the spinning mechanism 303 is spinning or after spinning has ceased. In addition, or instead, the cap 314 can include a first portion 342 pivotably or hingedly coupled to a second portion 344. The cap 314 can also be pivotably coupled to the lid 312. Accordingly, the cap 314 can allow access to the contents of the container 302 without being completely removed therefrom.

As demonstrated above, a disposable spinner flask according to an embodiment within the scope of this disclosure can be less expensive than existing disposable apparatuses, optimized for use with automated robotic cell culture systems, and facilitate easy access to the contents of the flask at all times including during or after operation.

One of ordinary skill in the art will also appreciate that the containers 102, 202, 302 may include various volumes depending on the intended application and the remainder of the disposable spinner flask components can be scaled to suit the container size, which for example can range from 100 milliliters to 100 liters, or any other suitable size.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A spinner flask comprising:
   a container having a mouth and a base, the container being shaped such that an interior of the container includes a first interior volume and a second interior volume contiguous the first interior volume, the first interior volume being generally cylindrical and the second interior volume protruding outwardly from the first interior volume and extending from a lower end of the container to the mouth;
   a cover assembly configured to be sealingly coupled to the mouth of the container and including an access port positioned to allow access to a lower end of the second interior volume near the base of the container during operation of the spinner flask; and
   a spinning mechanism positionable in the first interior volume, at least a portion of the spinning mechanism being rotatably mounted with respect to the container, at least when the cover assembly is coupled to the mouth of the container.

2. The spinner flask of claim 1 wherein the cover assembly includes a lid configured to be sealingly and removably coupled to the mouth of the container, and a cap configured to be coupled to the access port to cover the access port when the access port is not in use, the cap being configured to at least partially move away from the access port to allow access to the interior of the container.

3. The spinner flask of claim 2 wherein the cap is removably coupled to the access port and the lid further includes a first structural feature configured to retain the cap when the cap is removed from the access port.

4. The spinner flask of claim 2 wherein the cap includes a permeable membrane configured to prevent bacteria, viruses, and fungi from passing therethrough while allowing air exchange between the interior of the container and a surrounding environment.

5. The spinner flask of claim 1, wherein the cover assembly includes a cap configured to cover the access port and having at least one of a pierceable septum and a split septum to allow access to the interior of the container.

6. The spinner flask of claim 1 wherein the spinning mechanism includes at least one blade coupled to a magnetic device configured to rotate to induce rotation of the at least one blade when subjected to an external magnetic force.

7. The spinner flask of claim 6 wherein the spinning mechanism further includes a shaft having a first end and a second end, the shaft being coupled to the cover assembly toward the first end and to the at least one blade toward the second end.

8. The spinner flask of claim 7 wherein the shaft and the at least one blade are formed from a unitary body of material and the shaft is rotatably coupled to the cover assembly.

9. The spinner flask of claim 7 wherein the at least one blade is rotatably mounted to the shaft.

10. The spinner flask of claim 1 wherein the spinning mechanism includes a hub, a first blade, and at least a second blade, the first and second blades being mounted on opposing sides of the hub.

11. The spinner flask of claim 1 wherein the spinning mechanism includes a receptacle configured to removably receive and retain a magnetic device configured to rotate when subjected to an external magnetic force.

12. The spinner flask of claim 1 wherein the container is fabricated from injection moldable plastic.

13. The spinner flask of claim 1 wherein the container includes a teardrop cross-sectional shape at a lower end thereof in a region of the spinning mechanism such that, when the container is filled with fluid and the spinning mechanism rotates, a flow of fluid is generated in the lower end of the container and the flow is disrupted by the second interior volume.

14. The spinner flask of claim 1 wherein the first interior volume is larger than and contiguous the second interior volume and the access port is positioned such that a central longitudinal axis thereof extends in the second interior volume when the cover assembly is coupled to the mouth, and the second interior volume extending to the lower end of the container such that fluid is extractable from a region directly adjacent the spinning mechanism irrespective of whether the spinning mechanism is in operation.

15. The spinner flask of claim 14 wherein at least a portion of the spinning mechanism is positioned in the first interior volume.

16. The spinner flask of claim 1 wherein the mouth includes a return lip and the cover assembly includes a periphery configured to snap over the return lip for being sealingly coupled to the container.

17. The spinner flask of claim 1 wherein the spinning mechanism includes a magnetic member configured to rotate when subjected to an external magnetic force.

18. The spinner flask of claim 17 wherein the container and the magnetic member respectively include complementary structural features that engage each other to prevent lateral movement of the magnetic member as it rotates during operation.

19. The spinner flask of claim 1 wherein the container is fabricated from a polycarbonate material.

20. A spinner flask comprising:
a container having a mouth and a base, the container being shaped such that an interior of the container includes a first interior volume and a second interior volume contiguous the first interior volume, the first interior volume being generally cylindrical and the second interior volume protruding outwardly from the first interior volume and extending from a lower end of the container to the mouth;
means for covering the container configured to be sealingly coupled to the mouth of the container and including an access port to allow access to the interior volume at all times including during operation of the spinner flask; and
means for spinning a content of the container positioned in the first interior volume and rotatably mounted with respect to the container, at least when the covering means is coupled to the mouth of the container.

21. The spinner flask of claim 20 wherein the covering means includes a lid configured to be sealingly coupled to the mouth of the container such that an exterior periphery of the lid is flush with an exterior periphery of the container.

22. The spinner flask of claim 20 wherein the spinning means includes at least one of a motor, a magnet, and a blade.

23. The spinner flask of claim 20 wherein the container includes at least a first extension formed along at least a portion of a periphery of the container to define the second interior volume, the first extension contributing to an asymmetrical shape of the container and being positioned to allow access to the interior of the container at the lower end of the container without interfering with the spinning means.

24. The spinner flask of claim 23 wherein the covering means includes a lid having at least one access port including a central longitudinal axis substantially perpendicular to the base and extending through the asymmetric portion of the interior of the container.

25. The spinner flask of claim 24 wherein the container includes a second extension formed along at least a portion of the periphery of the container and extending from the mouth toward the base along at least a portion of the container to define a third interior volume, the lid further having a second access port including a central longitudinal axis substantially perpendicular to the base and extending through the third interior volume.

26. The spinner flask of claim 20 wherein the covering means includes a lid having at least one access port including a central longitudinal axis substantially perpendicular to, and intersecting, the base of the container.

27. The spinner flask of claim 20 wherein the covering means includes an access port having a permeable membrane on the cap configured to prevent bacteria, viruses, and fungi from passing therethrough while allowing air exchange between the interior of the container and a surrounding environment.

28. A spinner flask comprising:
an open-mouthed container having an interior defined by a first generally cylindrical interior volume and a second interior volume contiguous the first generally cylindrical interior volume, the second interior volume protruding outwardly from the first generally cylindrical volume and extending from a lower end of the container to a mouth of the container;
a cover assembly configured to be sealingly coupled to the mouth of the container and including an access port positioned to allow access to a lower end of the second interior volume near the lower end of the container; and
a spinning mechanism including a blade, the spinning mechanism configured to be rotatably mounted with respect to the container with the blade positioned in the first generally cylindrical interior volume of the container adjacent the lower end of the second interior volume such that, when the container is filled with fluid and the spinning mechanism rotates, a flow of fluid is generated in the lower end of the container and the flow is disrupted by the second interior volume.

* * * * *